United States Patent [19]

Terasawa et al.

[11] Patent Number: 5,019,503

[45] Date of Patent: May 28, 1991

[54] METHOD FOR PRODUCTION OF L-THREONINE

[75] Inventors: Masato Terasawa; Yukie Satoo; Hideaki Yukawa, all of Ibashiki, Japan

[73] Assignee: Mitsubishi Petrochemical Co., Ltd., Tokyo, Japan

[21] Appl. No.: 56,774

[22] Filed: Jun. 2, 1987

[30] Foreign Application Priority Data

Jun. 2, 1986 [JP] Japan ................................ 61-127776

[51] Int. Cl.⁵ ........................ C12P 13/08; C12N 1/20
[52] U.S. Cl. .................................... 435/115; 435/840; 435/252.1; 435/280
[58] Field of Search .................... 435/115, 252.1, 280, 435/840, 843, 861, 874

[56] References Cited

U.S. PATENT DOCUMENTS 3,099,604  7/1963  Kinoshita et al. .................. 435/115
3,527,671  9/1970  Zenk ................................... 435/280

FOREIGN PATENT DOCUMENTS 484846  6/1967  France ............................... 435/115

OTHER PUBLICATIONS

Dunmenil et al., *Eur. J. Appl. Microbiol.*, vol. 1, pp. 213-220, 1975.

Lynn et al., In Amino Acids Biosynthesis and Genetic Regulation, 1983, Addison-Wesley.
Goodfellow et al. *The Biology of Actinomycetes* 1984, Academic Press, pp. 77-79.
Bergey's Manual of Systematic Bacteriology, 1986, Williams and Wilkins, p. 1274.
Chemical Abstracts, vol. 99, Par 23, 5th Dec. 1983, p. 614, Abst. No. 193197v, Columbus, Ohio, U.S. & JP-A-58 129 990 Mar. 8, 1983.
Chemical Abstracts, vol. 85, Part II, 13th Jan. 1976, p. 411, Abstract No. 76311c, Columbus, Ohio, U.S., G. Dumenil et al.: Bioconversion from DL-Homoserine to L-Threonine., 1975, 1(3) 221-31.
Chemical Abstracts, vol. 56, Part 12, 10th Dec. 1962, p. 1962, Abstract No. 14746b, Columbus Ohio, U.S.; & JP-A-2 896/61 (Nissin Flour Milling Co., Ltd.) 11-0-4-1961.
Suzuki et al., *International Journal of Systematic Bacteriology*, vol. 31, pp. 131-138 (1981).

*Primary Examiner*—Douglas W. Robinson
*Assistant Examiner*—Irene Marx
*Attorney, Agent, or Firm*—Oblon, Spivak, McClelland, Maier & Neustadt

[57] ABSTRACT

A method for producting L-threonine is described, comprising subjecting L- or DL-homoserine to enzymatic reaction in an aqueous medium in the presence of cells of biotin-requiring microorganisms belonging to the genus Brevibacterium and harvesting L-threonine from the reaction mixture.

11 Claims, No Drawings

METHOD FOR PRODUCTION OF L-THREONINE

FIELD OF THE INVENTION

The present invention relates to a method for producing L-threonine. More particularly, this invention relates to a method for producing L-threonine from L- or DL-homoserine or even from D-homoserine with high efficiency.

L-threonine is an essential amino acid which plays a nutritionally vital role in man and animals and the demand for this amino acid as a medicament and a food or feed enriching agent has been increasing sharply in recent years.

BACKGROUND OF THE INVENTION

The commercial production of L-threonine has heretofore been conducted by fermentation processes because like other amino acids, L-threonine has stereoisomerism which makes the selective production of its L-isomer difficult. As examples of such fermentation processes, there may be mentioned the processes using amino acid-requiring strains (e.g Japanese Patent Publication Nos. 3319/71, 34193/71 and 34194/71) As to production processes relying on precursor fermentation, the processes using homoserine as a precursor (e.g. Japanese Patent Publication Nos. 2896/61, 6590/63 and 8715/68) can be mentioned.

As enzymatic production processes which are less costly in fixed cost and lend themselves better to production control than fermentation processes, the processes using glycine and acetaldehyde as precursors (e g. Japanese Laid-Open Patent Application Nos. 121491/81 and 116681/83), for instance, have been proposed but none of these processes have been successfully developed into commercial processes because of by-production of allothreonine.

Aside from these processes, it has been reported that L-threonine can be produced in a reaction medium containing DL-homoserine by means of various microbial cells [Shimura et al, Amino Acids, Vol 1, pp. 71-74, published by Association of Amino Acid Fermentation, (1959)]. However, by any of these known methods, the yield of L-threonine is not fully satisfactory.

On the other hand, not much research work for the commercial exploitation of DL-homoserine as a precursor has been reported This is because although the DL-form of homoserine has been chemically synthesized at comparatively low cost, the production of L-threonine requires a very high cost because L-threonine is formed only from L-homoserine but not from D-homoserine (Amino Acids, Vol 1, pp. 71-74, 1959).

SUMMARY OF THE INVENTION

The present inventors conducted an intensive research in hopes of resolving the above-mentioned problems and developing an enzymatic process for production of L-threonine using L- or DL-homoserine and even using D-homoserine as a principal starting material.

Thus, the present invention provides a method for producing L-threonine comprising subjecting L- or DL-homoserine to enzymatic reaction in aqueous medium in the presence of cells of biotin-requiring microorganisms belonging to the genus Brevibacterium and harvesting L-threonine from the reaction mixture.

In accordance with the present invention, L-threonine can be produced in high yield. Furthermore, the use of a synthetic complete medium containing ethanol and/or glucose as an enzymatic reaction aqueous medium not only results in a still higher yield of L-threonine but dispenses with the sterilization and other complicated procedures essential to fermentation processes, thus contributing greatly to the ease of production control.

Furthermore, when L- or DL-homoserine obtainable by racemizing D- or DL-homoserine in the presence of a racemizing enzyme is used as such in the method of this invention, the cells of a biotin-requiring strain of the genus Brevibacterium and the racemizing enzyme do not exert an adverse influence on each other, nor do they exert any unfavorable effect on the objective product L-threonine, with the result that L-threonine can be produced from commercially available, inexpensive DL- or D-homoserine with very high efficiency and productivity.

DETAILED DESCRIPTION OF THE INVENTION

The cells of biotin-requiring strains of microorganisms belonging to the genus Brevibacterium which are employed in the method of this invention may for example be the following strains, among which are L-threonine-producing strains included.

As ethanol-utilizing strains, there may be mentioned *Brevibacterium flavum* MJ-233 (FERM 1497), *Brevibacterium flavum* MJ-233-AB-41 (FERM BP-1498), *Brevibacterium flavum* MJ-233-ABT-11 (FERM BP-1500), *Brevibacterium flavum* MJ-233-ABD-21 (FERM BP-1499) and so on (these strains deposited at the Fermentation Research Institute, Agency of Industrial Science and Technology, 1-3, Higashi 1-chome, Tsukuba-shi, Ibaraki-ken 305, Japan, under the Budapest Treaty). Aside from these strains, *Brevibacterium ammoniagenes* ATCC 6871, *B. ammoniagenes* ATCC 13745, *B. ammoniagenes* ATCC 13746, *Brevibacterium divaricatum* ATCC 14020, and so on (these strains deposited at American Type Culture Collection, U.S.A.) can be mentioned.

Of these and other strains, those capable of assimilating ethanol are preferred. Particularly preferred are *Brevibacterium flavum* MJ-233, *Brevibacterium flavum* MJ-233-AB-41, *Brevibacterium flavum* MJ-233-ABT-11, and *Brevibacterium flavum* MJ-233-ABD-21.

The above-mentioned strain (FERM BP-1498) is an ethanol-utilizing mutant strain derived from the parent strain (FERM BP-1497) by imparting DL-α-aminobutyric acid resistance to the parent strain (See Japanese Patent Publication No. 28398/84, columns 3-4) The strain (FERM BP-1500) is a mutant strain having high L-α-aminobutyric acid transaminase activity as derived from the parent strain (FERM BP-1497) (See Japanese Laid-Open Patent Application No. 51998/87). The strain (FERM BP-1499) is a mutant strain having high D-α-aminobutyric acid deaminase activity as derived from the parent strain (FERM BP-1497) (See Japanese Laid-Open Patent Application No. 177993/86). For details of the parent strain (FERM BP-1497), reference can be made to Japanese Patent Publication No. 26755/82.

The "microbial cells" which are used in this invention include immobilized microbial cells The term "immobilized cells" means any of the preparations obtainable by the known immobilization techniques such as entrapment with acrylamide, alginic acid salts, carrageenan, etc., ion binding with DEAE-Sephadex, DEAE-cellulose and so on.

The method according to the present invention is conducted in aqueous medium This aqueous medium may for example be water or a buffer solution such as phosphate buffer, tris-HCl buffer and so on. More preferably, however, a synthetic complete medium containing ethanol and/or glucose is employed. This synthetic complete medium may be a known culture medium containing nitrogen sources, inorganic salts, etc as main components. Such nitrogen sources may for example be ammonia, ammonium sulfate, ammonium chloride, ammonium nitrate, urea and so on. The inorganic salts include potassium monohydrogen phosphate, potassium dihydrogen phosphate, magnesium sulfate, iron sulfate, manganese sulfate and so on.

The concentration of such nitrogen sources and/or inorganic salts may be similar to the concentration in the culture medium used for the cultivation of microorganisms and not subject to any specific limitation.

A typical example of such synthetic complete medium is an aqueous medium of pH 7.6 which contains 2 g/l of $(NH_4)_2SO_4$, 0.5 g/l of $KH_2PO_4$, 0.5 g/l of $K_2HPO_4$, 0.5 g/l of $MgSO_4.7H_2O$, 20 ppm of $FeSO_4.7H_2O$ and 20 ppm of $MnSO_4.4-6H_2O$.

The synthetic complete medium used in the present invention is one that does not contain biotin or any biotin-containing natural material Amino acids, vitamins, carbohydrates, etc. with defined chemical structures other than biotin can be incorporated The level of addition of ethanol and/or glucose to such a synthetic complete medium is about 1 to 20 volume percent for ethanol and about 0.5 to 20 weight percent for glucose. When both ethanol and glucose are added, each is used within the above-mentioned range.

The concentration of L- or DL-homoserine in the reaction system is generally in the range of 0.1 to 20 percent (w/v). While there is no limitation on the amount of microbial cells, the cells can be used generally at the concentration of 1 to 50 percent (w/v).

The enzymatic reaction is carried out at a temperature of about 20° to 50° C., preferably about 30° to 40° C., generally for about 10 to 72 hours.

In the method according to the present invention, it is advantageous to use the products obtained by subjecting DL-homoserine which is commercially available at low cost or the D-homoserine or D-homoserine-rich DL-homoserine which has remained as an unreacted residue in the enzymatic reaction to racemization in the presence of a microorganism capable of racemizing D-homoserine without utilizing L-threonine as the substrate, a processed matter thereof or an immobilized preparation thereof. Examples of the processed matter derived from the microorganism include a crushed microorganism, an enzyme extracted therefrom, and the like.

The microorganism which is capable of racemizing D-homoserine without utilizing L-threonine as the substrate may for example be *Pseudomonas putida* IFO 12996 and so on (the strain deposited at Institute for Fermentation, Osaka, 17–85, Juso-honmachi 2-chome, Yodogawa-ku, Osaka 532, Japan).

The above-mentioned microorganism or an equivalent thereof which is capable of racemizing D-homoserine may be added at the start of the enzymatic reaction according to this invention or in the course of the enzymatic reaction. As an alternative, the microorganism or equivalent can be used for racemization in a reaction system independent of the enzymatic reaction system.

The above-mentioned microorganism capable of racemizing D-homoserine, a processed matter thereof or an immobilized preparation thereof is used generally in a proportion of about 0.1 to 50 weight percent, preferably in a proportion of about 1 to 30 weight percent.

The L-threonine produced in such an enzymatic reaction mixture can be easily separated and purified by treatment with an ion exchange resin, precipitation and other techniques.

The two kinds of microorganisms, namely a microorganisms capable of producing L-threonine from homoserine and a microorganism capable of racemizing only D-homoserine without utilizing L-threonine as a substrate can be obtained by the following cultural procedures.

As the carbon sources to be employed in the culture of these microorganisms, there can be utilized glucose, ethanol, methanol, spent molasses, and so on. As the nitrogen sources, such materials as ammonia, ammonium sulfate, ammonium chloride, ammonium nitrate, urea and so on can be utilized. These carbon and nitrogen sources may be used alone or in combination.

The inorganic salts which can be incorporated in the medium include potassium monohydrogen phosphate, potassium dihydrogen phosphate, magnesium sulfate and so on. In addition to these medium components, such other nutrients as peptone, meat extract, yeast extract, corn steep liquor, casamino acids, various kinds of vitamins such as biotin etc. and so on can be incorporated.

The cultivation is conducted under aerobic conditions, for example, by spinned culture, shake culture and so on, at an incubation temperature in the range of about 20° to 40° C., preferably about 25° to 35° C. The cultivation is carried out at pH about 5 to 10, preferably at pH about 7 to 8. For pH control during cultivation, an acid and/or an alkali can be employed.

The concentration of ethanol at initiation of cultivation is preferably about 1 to 5 volume percent, more preferably about 2 to 3 volume percent. The incubation period is 2 to 9 days, preferably 4 to 7 days.

From the culture broth thus obtained, the cells are collected by filtration or centrifugation, washed with water or a suitable buffer solution and used in the enzymatic reaction according to the present invention.

The present invention will be explained in greater detail with reference to the following examples, but the present invention should not be construed as being limited thereto. In these examples, the qualitative identification of L-threonine was performed by Rf value of paper chromatography, mobility of electrophoresis and microbial activity on microbioassay. The quantitative estimation of L-threonine was performed by microbioassay using *Leuconostoc mesenteroides* ATCC 8042 as the test organism in combination with high performance liquid chromatography (Shimadzu Model LC-5A) Unless otherwise indicated, the percent (%) indications in the Examples stand for weight percents.

EXAMPLE 1

A 500 ml conical flask was filled with 100 ml of a seed culture medium composed of 0.4% urea, 1.4% ammonium sulfate, 0.05% $KH_2PO_4$, 0.05% $K_2HPO_4$, 0.05% $MgSO_4.7H_2O$, 2 ppm $CaCl_2.2H_2O$, 2 ppm $FeSO_4.7H_2O$, 2 ppm $MnSO_4.4-6H_2O$, 2 ppm $ZnSO_4.7H_2O$, 2 ppm NaCl, 200 µg/l biotin, 100 µg/l thiamine hydrochloride, 0.1% casamino acids and 0.1% yeast extract After sterilization (pH 7.0 after sterilization), the flask was inoculated with *Brevibacterium flavum* MJ-233 (FERM BP-1497) and, then 2 ml of ethanol was aseptically added. Incubation was carried out under shaking at 30° C. for 2 days.

A 2-liter aerobic spinner culture tank was charged with 1000 ml of a culture medium composed of 2.3% ammonium sulfate, 0.05% $KH_2PO_4$, 0.05% $K_2HPO_4$, 0.05% $MgSO_4.7H_2O$, 20 ppm $FeSO_4.7H_2O$, 20 ppm $MnSO_4.nH_2O$, 200 µg/l biotin, 100 µg/l thiamine hydrochloride, 0.3% casamino acids and 0.3% yeast extract After sterilization (120° C., 20 minutes), 20 ml of ethanol and 20 ml of the above seed culture were added and incubation was conducted under the conditions of 1000 rpm, 1 vvm (volume of air per volume of liquid per minute) aeration, 33° C. and pH 7.6 for 48 hours.

During the cultivation, ethanol was added intermittently at intervals of about 1 to 2 hours using care so that the ethanol concentration of the medium would not exceed 2 volume %.

After completion of cultivation, the cells were collected by centrifugation of the broth (300 ml) and rinsed with desalted distilled water twice. The washed cells were suspended in 1000 ml of a reaction medium composed of 2 g/l $(NH_4)_2SO_4$, 0.5 g/l $KH_2PO_4$, 0.5 g/l $K_2HPO_4$, 0.5 g/l $MgSO_4.7H_2O$, 20 ppm $FeSO_4.7H_2O$, 20 ppm $MnSO_4.4-6H_2O$, 100 µg/l thiamine hydrochloride and 2 g/l DL-homoserine (pH 7.6). This suspension and 20 ml of ethanol were charged into a two-liter aerobic spinner culture tank and the reaction was conducted under the conditions of 300 rpm, 0.1 vvm aeration, 37° C. and pH 7.0 for 10 hours.

After completion of the reaction, the reaction mixture was centrifuged at 4000 rpm for 15 minutes at 4° C. to remove the cells and the L-threonine in the supernatant was assayed In addition, a 500 ml portion of the reaction mixture was passed through a column of strongly acidic cation exchange resin ($H^+$-form) to adsorb the L-threonine and after the column was rinsed with water, elution was carried out with 0.5N aqueous ammonia. The fractions rich in L-threonine were pooled and concentrated and the concentrate was treated with cold ethanol to give crystals of L-threonine. The results are shown in Table 1.

TABLE 1

| Output of L-threonine (mg/l) | Purified Yield of L-threonine (mg) |
| --- | --- |
| 280 | 94 |

The above procedure was repeated except that 200 µg/l of biotin was added to the reaction medium The output of L-threonine was 180 mg/l.

EXAMPLE 2

*Brevibacterium flavum* MJ-233-AB-41 (FERM BP-1498) was grown under the same conditions as in Example 1 and the subsequent reaction was also conducted in the same manner as in Example 1. Then, in the same manner as in Example 1, L-threonine in the supernatant was assayed and crystals of L-threonine were precipitated. The results are shown in Table 2.

TABLE 2

| Output of L-threonine (mg/l) | Purified Yield of L-threonine (mg) |
| --- | --- |
| 290 | 97 |

EXAMPLE 3

*Brevibacterium flavum* MJ-233-ABT-11 (FERM BP-1500) was grown under the same conditions as in Example 1 and the subsequent reaction was conducted also in the same manner as in Example 1. Then, L-threonine in the supernatant was assayed and crystals of L-threonine were precipitated by the same procedure as described in Example 1. The results are shown in Table 3.

TABLE 3

| Output of L-threonine (mg/l) | Purified Yield of L-threonine (mg) |
| --- | --- |
| 288 | 95 |

EXAMPLE 4

*Brevibacterium flavum* MJ-233-ABD-21 (FERM BP-1499) was grown under the same conditions as in Example 1 and the subsequent reaction was conducted also in the same manner as in Example 1. Then, L-threonine in the supernatant was assayed and crystals of L-threonine were precipitated by the same procedure as described in Example 1. The results are shown in Table 4.

TABLE 4

| Output of L-threonine (mg/l) | Purified Yield of L-threonine (mg) |
| --- | --- |
| 275 | 90 |

EXAMPLE 5

The procedure of Example 1 was repeated except that glucose was added in lieu of ethanol in the enzymatic reaction medium. The level of addition of glucose was 2 weight %. The L-threonine content of the supernatant and the purified yield of L-threonine are shown in Table 5.

TABLE 5

| Output of L-threonine (mg/l) | Purified Yield of L-threonine (mg) |
| --- | --- |
| 285 | 95 |

The same procedure as above was followed except that 200 µg/l of biotin was added to the reaction medium. The output of L-threonine was 185 mg/l.

REFERENCE EXAMPLE 1

(Preparation of D-homoserine racemizing enzyme)

A 500 ml conical flask was filled with 100 ml of a medium A, the composition of which is shown below, and after sterilization at 120° C. for 15 minutes, the medium was inoculated with a loopful of *Pseudomonas putida* IFO 12996 and shake culture was conducted at 30° C. for 24 hours. Then, a 5-liter conical flask was charged with 1 l of the same medium A as above and after sterilization at 120° C. for 15 minutes, the medium was inoculated with 20 ml of the above preculture and incubated under shaking at 30° C. for 24 hours.

After completion of cultivation, the cells were collected by centrifugation of the broth (1 liter) and suspended in pure water to give 20 ml of a cell suspension. To this cell suspension were added 4.2 g of acrylamide, 0.28 g of N,N'-methylenebisacrylamide, 3 ml of 4% β-(dimethylamino)propionitrile and 2 ml of 2% potassium perchlorate and the mixture was allowed to stand for 15 minutes to give a cell-containing polymer. This polymerization reaction product was pulverized and rinsed with pure water to give 30 g of immobilized cells for use as a D-homoserine racemizing enzyme source. The cell immobilization procedure was aseptically performed.

| Medium A | |
|---|---|
| Meat extract | 1% |
| Peptone | 1% |
| NaCl | 0.5% |
| pH | 7.2 |

EXAMPLE 6

A 500 ml conical flask was filled with 50 ml of a medium composed of 0.4% urea, 1.4% ammonium sulfate, 0.05% $KH_2PO_4$, 0.05% $K_2HPO_4$, 0.05% $MgSO_4.7H_2O$, 2 ppm $CaCl_2.2H_2O$, 2 ppm $FeSO_4.7H_2O$, 2 ppm $MnSO_4.4-6H_2O$, 2 ppm $ZnSO_4.7H_2O$, 2 ppm NaCl, 200 μg/l biotin, 100 μg/l thiamine hydrochloride, 0.1% casamino acids, and 0.1% yeast extract After sterilization (pH 7.0 after sterilization), the flask was inoculated with *Brevibacterium flavum* MJ-233 (FERM BP-1497). Then, 1.5 ml of ethanol was aseptically added and shake culture was conducted at 30° C. for 3 days. After completion of cultivation, the cells were harvested by 15-minute centrifugation at 4000 rpm for use as an enzyme source for the production of L-threonine from homoserine.

To 100 ml of a reaction medium containing 1 mg of DL-homoserine, 5 μg of pyridoxal phosphate, 100 μmoles of phosphate buffer and 10 mg of ethanol per milliliter (pH 7.0) were added 5 g of the above cells and 20 g of the immobilized cells prepared in accordance with Reference Example 1 and the reaction was conducted at 37° C. for 16 hours The overall output of L-threonine was 60 mg.

The reaction mixture was filtered to remove the cells and impurities and the filtrate was passed through a column of strongly acidic cation exchange resin (H+- form) to adsorb the L-threonine. After the column was rinsed with water, elution was carried out with 0.5N aqueous ammonia. The fractions rich in L-threonine were pooled and concentrated and the residue was treated with cold ethanol to give 36 mg crude crystals of L-threonine. In contrast, when the immobilized cells of Reference Example 1 were not added, the overall output of L-threonine was 28 mg.

EXAMPLE 7

The enzymatic reaction was conducted in the same manner as in Example 1 except that 2 g/l of D-homoserine was used in lieu of DL-homoserine in the reaction medium and 10 g of the immobilized cells according to Reference Example 1 were added to the reaction system. After the reaction, in the same manner as in Example 1, the cells were removed and L-threonine in the supernatant was assayed The output of L-threonine was 42 mg/l.

As a control, the above enzymatic reaction was repeated except that the immobilized D-homoserine-racemizing cells were not added to the reaction system. In this case, the L-threonine content of the supernatant was up to 1 mg/l.

While the invention has been described in detail and with reference to specific embodiments thereof, it will be apparent to one skilled in the art that various changes and modifications can be made therein without departing from the spirit and scope thereof

What is claimed is:

1. A process for producing L-threonine, comprising:
    (i) subjecting L- or DL-homoserine to enzymatic reaction with glucose or ethanol, in a biotin-free synthetic complete medium in the presence of cells of biotin-requiring microorganism *Brevibacterium flavum* MJ-233 (FERM BP-1497) or mutant strain thereof capable of producing L-threonine, and
    (ii) harvesting L-threonine from the reaction mixture.

2. The process as claimed in claim 1, wherein said biotin-requiring microorganism is one member selected from the group consisting of:
    *Brevibacterium flavum* MJ-233 (FERM BP-1497),
    *Brevibacterium flavum* MJ-233-AB-41 (FERM BP-1498),
    *Brevibacterium flavum* MJ-233-ABT-11 (FERM BP-1500), and
    *Brevibacterium flavum* MJ-233-ABD-21 (FERM BP-1499).

3. The process as claimed in claim 1, wherein said biotin-free synthetic complete medium comprises a D-homoserine-racemizing enzyme in the form of (1) cells of *Pseudomonas putida* IFO 12996, (2) crushed cells of said *Pseudomonas putida*, (3) a D-homoserine-racemizing enzyme extracted from said *Pseudomonas putida*, or (4) an immobilized preparation thereof.

4. The process of claim 1, comprising using L-homoserine.

5. The process of claim 1, comprising using DL-homoserine.

6. The process of claim 1, comprising subjecting L- or DL-homoserine to enzymatic reaction with glucose.

7. The process of claim 1, comprising subjecting L- or DL-homoserine to enzymatic reaction with ethanol.

8. The process of claim 2, comprising using *Brevibacterium flavum* MJ-233 (FERM BP-1497).

9. The process of claim 2, comprising using *Brevibacterium flavum* MJ-233-AB-41 (FERM BP-1498).

10. The process of claim 2, comprising using *Brevibacterium flavum* MJ-233-ABT-11 (FERM BP-1500).

11. The process of claim 2, comprising using *Brevibacterium flavum* MJ-233-ABD-21 (FERM BP-1499).

* * * * *